United States Patent
Crane et al.

(10) Patent No.: US 8,022,275 B2
(45) Date of Patent: Sep. 20, 2011

(54) MAIZE PROMOTER ACTIVE IN SILK AND PERICARP TISSUES

(76) Inventors: Virginia C. Crane, Des Moines, IA (US); Jeanne Sandahl, West Des Moines, IA (US); Carl R. Simmons, Des Moines, IA (US)

( * ) Notice: Subject to any disclaimer, the term of this patent is extended or adjusted under 35 U.S.C. 154(b) by 100 days.

(21) Appl. No.: 12/197,389

(22) Filed: Aug. 25, 2008

(65) Prior Publication Data

US 2009/0055966 A1 Feb. 26, 2009

Related U.S. Application Data

(60) Provisional application No. 60/957,503, filed on Aug. 23, 2007.

(51) Int. Cl.
*A01H 1/00* (2006.01)
*C07H 21/04* (2006.01)
*C12N 15/00* (2006.01)

(52) U.S. Cl. ........ 800/295; 435/6.1; 435/69.1; 435/468; 435/419; 435/320.1; 536/24.1; 800/278

(58) Field of Classification Search ............ 435/6, 69.1, 435/468, 419, 320.1, 6.1; 536/24.1; 800/278, 800/295; 530/370
See application file for complete search history.

(56) References Cited

U.S. PATENT DOCUMENTS

2005/0155114 A1* 7/2005 Hinchey ........................ 800/288

OTHER PUBLICATIONS

Whitelaw et al., EST Database, Acc. No. CG225354, direct submission, Aug. 22, 2003, see Result 1.*
Nielsen, et al., Identification of prokaryotic and eukaryotic signal peptides and prediction of their cleavage sites, Protein Engineering, (1997), 10(1):1-6.
Jean-Claude Kader, Lipid-Transfer Proteins in Plants, Annu. Rev. Plant Physiol. Plant Mol. Biol., (1996), 47:627-654.
Federico, et al., The complex developmental expression of a novel stress-responsive barley *Ltp* gene is determined by a shortened promoter sequence, Plant Mol. Biol., (2005), 57:35-51.
Carvalho, et al., Role of plant lipid transfer proteins in plant cell physiology-A concise review, Peptides, (2007), 28:1144-1153.
Boutrot, et al., The *Triticum aestivum* non-specific lipid transfer protein (*TaLtp*) gene family: comparative promoter activity of six *TaLtp* genes in transgenic rice, Planta (2006).
Database EMBL (Online), *Zea mays* chromosome 3 clone CH201-22C20, Database accession No. AC184173 (Jul. 25, 2007).
Database EMBL (Online), OG2AH63TV ZM_0.7_1.5_KB *Zea mays* genomic clone ZMMBMa0742L06, genomic survey sequence, Database accession No. CG225354 (2002).

* cited by examiner

*Primary Examiner* — Phuong T Bui
(74) *Attorney, Agent, or Firm* — Pioneer Hi-Bred International, Inc.; Kathryn K. Lappegard

(57) ABSTRACT

The present disclosure provides compositions and methods for regulating expression of heterologous nucleotide sequences in a plant. Compositions include a novel nucleotide sequence for a tissue-preferred maize promoter. A method for expressing a heterologous nucleotide sequence in a plant using the promoter sequence disclosed herein is provided. The method comprises stably incorporating into the genome of a plant cell a nucleotide sequence operably linked to the tissue-preferred promoter of the present invention and regenerating a stably transformed plant that expresses the nucleotide sequence.

13 Claims, 1 Drawing Sheet

FIGURE 1

```
                   1                                                50
SEQ ID NO: 6    (1) ----------MAAPKLATLALAVLLAATVVAPPAAVRAAMSCSTVYSTLMPC
SEQ ID NO: 9    (1) ----------MAPRCATLAVVVLVAAVVAPTAVRAAISCSAVYNTLMPC
SEQ ID NO: 10   (1) MVPAARSGWPAAAAVLVVVLVLSSPPGTSTVVARAALSCSTVYNTLLPC
SEQ ID NO: 11   (1) ----------MAAPRGAALVLAMVLAAMVVAPPVTVRAAISCSAVYSTLMPC
SEQ ID NO: 12   (1) ----------MAAPRGAALVLAMVLAAMVVAPPATVHAAISCSTVYSTLMPC
SEQ ID NO: 13   (1) ----------MAAPRGAALVLAMVLAAMLVAPPATVH-AISCSTVYSTLMPC
SEQ ID NO: 14   (1) ----------MAAPRGAALVLAMVLAAMLVAPPATVH-AISCSTVYSTLMPC
SEQ ID NO: 15   (1) ----------MAAPRGAALVLAMVLAAMLVAPPATVH-AISCSTVYSTLMPC 51                                               100
SEQ ID NO: 6   (43) LPFVQMGGAMPPQPCCGGIRSLLQQANNTPDRRTICGCLKNVANGANGSG
SEQ ID NO: 9   (42) LPYVQAGGTV-PRACCGGIQSLLAAANNTPDRRTICGCLKNVANGASG-G
SEQ ID NO: 10  (51) LPYVQSGGAV-PAACCGGIRSVVAAARTTADRRAACTCLKNVAAGAAG-G
SEQ ID NO: 11  (43) LQYVQQGGTP-ARGCCAGIQNLLAEANNSPDRRTICGCLKNVANAAPG-G
SEQ ID NO: 12  (43) LQYVQQGGSP-ARGCCTGIQNLLAEANNSPDRRTICGCLKNVANGASG-G
SEQ ID NO: 13  (42) LQYVQQGGSP-ARGCCTGIQNLLAEANNSPDRRTICGCLKNVANGASG-G
SEQ ID NO: 14  (42) LQYVQQGGSP-ARGCCTGIQNLLAEANNSPDRRTICGCLKNVANGASG-G
SEQ ID NO: 15  (42) LQYVQQGGSP-ARGCCTGIQNLLVEAANNSPDRRTICGCLENVANGASG-G 101                                              140
SEQ ID NO: 6   (93) TYISRAAALPSKCGVALPYKISTNVNCNTIN-----------------
SEQ ID NO: 9   (90) PYITRAAALPSKCNVSLPYKISTSVNCNAIN-----------------
SEQ ID NO: 10  (99) PYISRAAGLPGRCGVSVPFKISPNVNCNAYVKTKNQINLY
SEQ ID NO: 11  (91) SEITRAAALPSKCNVNLPYKISPSVDCNSIH-----------------
SEQ ID NO: 12  (91) PYITRAAALPSKCNVALPYKISPSVDCNSIH-----------------
SEQ ID NO: 13  (90) PYITRAAALPSKCNVALPYKISPSVDCNSIH-----------------
SEQ ID NO: 14  (90) PYITRAAALPSKCNVALPYKISPSVDCNSIH-----------------
SEQ ID NO: 15  (90) PYITRAAALPSKCNVALPYKISPSVDCNSIH-----------------
```

MAIZE PROMOTER ACTIVE IN SILK AND PERICARP TISSUES

CROSS REFERENCE TO RELATED APPLICATIONS

This application claims the benefit of U.S. Provisional Application No. 60/957,503, filed on Aug. 23, 2007, which is herein incorporated by reference in its entirety.

FIELD OF THE INVENTION

The present invention relates to the field of plant molecular biology, more particularly to regulation of gene expression in plants.

BACKGROUND OF THE INVENTION

Recent advances in plant genetic engineering have enabled the engineering of plants having improved characteristics or traits, such as disease resistance, insect resistance, herbicide resistance, enhanced stability or shelf-life of the ultimate consumer product obtained from the plants and improvement of the nutritional quality of the edible portions of the plant. Thus, one or more desired genes from a source different than the plant, but engineered to impart different or improved characteristics or qualities, can be incorporated into the plant's genome. One or more new genes can then be expressed in the plant cell to exhibit the desired phenotype such as a new trait or characteristic.

The proper regulatory signals must be present and be in the proper location with respect to the gene in order to obtain expression of the newly inserted gene in the plant cell. These regulatory signals may include a promoter region, a 5' non-translated leader sequence and a 3' transcription termination/polyadenylation sequence.

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

Expression of heterologous DNA sequences in a plant host is dependent upon the presence of an operably linked promoter that is functional within the plant host. The type of promoter sequence chosen is based on when and where within the organism expression of the heterologous DNA is desired. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins. In the case of fighting plant pests, it is also desirable to have a promoter which is induced by plant pathogens, including plant insect pests, nematodes or disease agents such as a bacterium, virus or fungus. Contact with the pathogen will induce activation of transcription, such that a pathogen-fighting protein will be produced at a time when it will be effective in defending the plant. A pathogen-induced promoter may also be used to detect contact with a pathogen, for example by expression of a detectable marker, so that the need for application of pesticides can be assessed. A plant cell containing an inducible promoter may be exposed to an inducer by externally applying the inducer to the cell or plant such as by spraying, watering, heating, or by exposure to the operative pathogen.

A constitutive promoter is a promoter that directs expression of a gene throughout the various parts of a plant and continuously throughout plant development. Examples of some constitutive promoters that are widely used for inducing the expression of heterologous genes in transgenic plants include the nopaline synthase (NOS) gene promoter, from *Agrobacterium tumefaciens*, (U.S. Pat. No. 5,034,322), the cauliflower mosaic virus (CaMv) 35S and 19S promoters (U.S. Pat. No. 5,352,605), those derived from any of the several actin genes, which are known to be expressed in most cells types (U.S. Pat. No. 6,002,068), and the ubiquitin promoter (Christensen et al. (1989) *Plant Mol. Biol.* 12:619-632 and Christensen et al. (1992) *Plant Mol. Biol.* 18:675-689), which is a gene product known to accumulate in many cell types.

Additional regulatory sequences upstream and/or downstream from the core promoter sequence may be included in expression constructs of transformation vectors to bring about varying levels of expression of heterologous nucleotide sequences in a transgenic plant. Genetically altering plants through the use of genetic engineering techniques to produce plants with useful traits thus requires the availability of a variety of promoters.

In order to maximize the commercial application of transgenic plant technology, it is important to direct the expression of the introduced DNA in a site-specific manner. For example, it is desirable to produce toxic defensive compounds in tissues subject to pathogen attack, but not in tissues that are to be harvested and eaten by consumers. By site-directing the synthesis or storage of desirable proteins or compounds, plants can be manipulated as factories, or production systems, for a tremendous variety of compounds with commercial utility. Cell-specific promoters provide the ability to direct the synthesis of compounds, spatially and temporally, to highly specialized tissues or organs, such as roots, leaves, vascular tissues, embryos, seeds, or flowers.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Since the patterns of expression of a chimeric gene (or genes) introduced into a plant are controlled using promoters, there is an ongoing interest in the isolation and identification of novel promoters which are capable of controlling expression of a chimeric gene (or genes).

SUMMARY OF THE INVENTION

Compositions and methods for regulating gene expression in a plant are provided. Compositions comprise novel nucleotide sequences for a promoter that initiates transcription in a tissue-specific manner. More particularly, a transcriptional initiation region isolated from a plant lipid transfer gene is provided. Further embodiments of the invention comprise the nucleotide sequences set forth in SEQ ID NOs:1-4 and the plant promoter sequence deposited as Patent Deposit No. NRRL B-50159 with the Agricultural Research Service (ARS) Culture Collection, housed in the Microbial Genomics and Bioprocessing Research Unit of the National Center for Agricultural Utilization Research (NCAUR), under the Budapest Treaty provisions. Three promoter fragments, SEQ NOs 1-3, were each tested immediately 5' of the ZM-027 5'UTR, SEQ ID:4. The compositions of the embodiments further comprise nucleotide sequences having at least 70% sequence identity to the sequences set forth in SEQ ID NOs: 1-4, and which drive tissue-preferred expression of an operably linked nucleotide sequence. Also included are nucleotide sequences that hybridize under stringent conditions to either the sequences set forth in SEQ ID NO: 1-4. or to the plant promoter sequence deposited in bacterial hosts as Patent Deposit No. NRRL B-50159, or their complements.

Compositions also include DNA constructs comprising a promoter of the embodiments operably linked to a heterologous nucleotide sequence of interest wherein said promoter is capable of driving expression of said nucleotide sequence in a plant cell and said promoter comprises the nucleotide sequences of the embodiments. The embodiments further provide expression vectors, and plants or plant cells having stably incorporated into their genomes a DNA construct mentioned above. Additionally, compositions include transgenic seed of such plants.

Methods of the embodiments comprise a means for selectively expressing a nucleotide sequence in a plant, comprising transforming a plant cell with a DNA construct, and regenerating a transformed plant from said plant cell, said DNA construct comprising a promoter and a heterologous nucleotide sequence operably linked to said promoter, wherein said promoter initiates tissue-specific transcription of said nucleotide sequence in a plant cell. In this manner, the promoter sequences are useful for controlling the expression of operably linked coding sequences in a tissue-specific manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel function or product in the plant. For example, a heterologous nucleotide sequence that encodes a gene product that confers pathogen, herbicide, salt, cold, drought, or insect resistance is encompassed.

In a further aspect, disclosed methods relate to a method for modulating expression in selected tissues of a stably transformed plant comprising the steps of (a) transforming a plant cell with a DNA construct comprising the promoter of the embodiments operably linked to at least one nucleotide sequence; (b) growing the plant cell under plant growing conditions and (c) regenerating a stably transformed plant from the plant cell wherein expression of the nucleotide sequence alters the phenotype of the plant.

BRIEF DESCRIPTION OF THE DRAWINGS

FIG. 1. Alignment of ZM-027 propeptide sequence with related sequences in the public domain. Designations for the wheat Ltps are found in Boutrot et al. (2007) *Planta* 225:843-862. Sequence identifier numbers are included next to each sequence, and GenBank identifier numbers are provided in the sequence listing accompanying this application.

DETAILED DESCRIPTION OF THE INVENTION

The compositions of the embodiments comprise novel nucleotide sequences for plant promoters, particularly a tissue-preferred promoter for a maize gene, more particularly, the maize ZM-027 promoter. In particular, the embodiments provide for isolated nucleic acid molecules comprising the nucleotide sequences set forth in SEQ ID NOs:1-4 and the plant promoter sequence deposited in bacterial hosts as Patent Deposit No. NRRL B-50159 on Jul. 22, 2008 and fragments, variants, and complements thereof.

A deposit of the maize "ZM-027" promoter was made on Jul. 22, 2008 with the Agricultural Research Service (ARS) Culture Collection, housed in the Microbial Genomics and Bioprocessing Research Unit of the National Center for Agricultural Utilization Research (NCAUR), under the Budapest Treaty provisions. The deposit was given the following accession number: NRRL B-50159. The address of NCAUR is 1815 N. University Street, Peoria, Ill., 61604. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112. The deposit will irrevocably and without restriction or condition be available to the public upon issuance of a patent. However, it should be understood that the availability of a deposit does not constitute a license to practice the subject invention in derogation of patent rights granted by government action.

The promoter sequences of the embodiments are useful for expressing operably linked nucleotide sequences in a tissue-preferred manner. Particularly, the promoter of the embodiments, when used in conjunction with the maize AdhI intron, and including the native 5' UTR, drives expression at high levels in several different tissues of the plant, but not constitutively. The pattern of expression is of interest because it includes tissues which are affected by the commercially important ear rot pathogens, *Fusarium verticillioides, F. graminearum* and *Diplodia maydis*. It also provides a unique, genetic regulatory element capable of directing expression to pericarp tissue for a variety of trait purposes. The promoter drives low levels of expression in the silk, and very high levels in the pericarp.

The sequences of the embodiments also find use in the construction of expression vectors for subsequent transformation into plants of interest, as molecular markers, and the like. The ZM-027 promoter sequences of the embodiments direct expression of operably linked nucleotide sequences in a tissue-preferred manner. Therefore, the ZM-027 promoter sequences find use in the tissue-preferred expression of an operably linked nucleotide sequence of interest. The specific method used to obtain the ZM-027 promoter of the present embodiments is described in Example 1 appearing in the Examples section of this application.

The embodiments encompass isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is essentially free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The ZM-027 promoter drives the endogenous expression of a maize gene (SEQ ID NO: 5) that is predicted to encode a class II non-specific lipid transfer protein (SEQ ID NO: 6). Plant lipid transfer proteins (LTPs) are positively-charged peptides grouped into two classes based on apparent molecular mass of the mature forms, either about 7 or 10 kDa. Their classification as lipid transfer proteins results from the observation that they can bind hydrophobic molecules and facilitate the transfer of phospholipids between membranes in vitro. Both classes of LTPs are characterized by eight conserved cysteine residues. Nonspecific LTPs (nsLTPs) are typically synthesized as propeptides containing a signal peptide which targets the mature peptide to the secretory pathway. The function of most LTPs in plants is unclear, although subcellular localization may provide clues. Plant LTPs are found in the apoplast, glyoxysome, protein granules in seeds and in protein storage vacuoles. LTP expression has been found to be under both developmental and environmental regulation. In particular, expression during defense responses and in floral tissues is a common theme. It has been proposed that plant LTPs function in defense signalling, cutin formation, as food allergens and as antimicrobials (see Kader, J-C. (1996) *Ann. Rev. Plant Physiol.* Plant Mol. Biol. 47:627-54 and de Oliveira Carvalho and Gomes (2007) *Peptides* 28:1144-53 for review).

In silico analysis of the predicted coding sequence for ZM-027 places this gene squarely in class I of the nsLTPs. These have molecular masses of about 10 kDa and isoelectric points (pIs) of 9-10. The calculated molecular mass for the mature ZM-027 peptide is 9.9 kDa and its pI is 9.1. A TBLASTX search against the nonredundant nucleotide database of the NCBI (National Center for Biotechnology Information) reveals a number of homologs within monocots other than maize. Identities range from 77-67% and homology is significant across the entire sequence. An alignment of ZM-027 and related amino acid sequences is presented in FIG. 1. Analysis of the propeptide sequence using SignalP (V1.1 with neural networks, initially described in Nielsen et al. 1997 Protein Engineering 10:1-6) predicts a signal peptide consisting of amino acids 1-28 (SEQ ID NO: 8). The mature peptide consists of 95 amino acids (SEQ ID NO: 7).

The compositions of the embodiments include isolated nucleic acid molecules comprising the promoter nucleotide sequences set forth in SEQ ID NOs:1-4. The term "promoter" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements such as those responsible for tissue and temporal expression of the coding sequence, enhancers, and the like. See particularly Australian Patent No. AU-A-77751/94 and U.S. Pat. Nos. 5,466,785 and 5,635,618. In the same manner, the promoter elements that enable expression in desired tissues, can be identified, isolated, and used with other core promoters to confer tissue-preferred expression. In this aspect of the embodiments, a "core promoter" is intended to mean a promoter without promoter elements.

In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of this disclosure, a post-transcriptional regulatory element may include elements that are active following transcription initiation, for example translational and transcriptional enhancers, translational and transcriptional repressors, and mRNA stability determinants.

The regulatory elements, or fragments thereof, of the embodiments may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the embodiments may be operatively associated with constitutive, inducible, or tissue preferred promoters or fragments thereof, to modulate the activity of such promoters within desired tissues within plant cells.

The maize tissue-preferred promoter sequences of the embodiments, when assembled within a DNA construct such that the promoter is operably linked to a nucleotide sequence of interest, enable expression of the nucleotide sequence in the cells of a plant stably transformed with this DNA construct. The term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remain in the proper reading frame. In this manner, the nucleotide sequences for the promoters of the embodiments are provided in DNA constructs along with the nucleotide sequence of interest, typically a heterologous nucleotide sequence, for expression in the plant of interest. The term "heterologous nucleotide sequence" is intended to mean a sequence that is not naturally operably linked with the promoter sequence. While this nucleotide sequence is heterologous to the promoter sequence, it may be homologous, or native; or heterologous, or foreign, to the plant host.

It is recognized that the promoters of the embodiments thereof may be used with their native coding sequences to increase or decrease expression, thereby resulting in a change in phenotype of the transformed plant.

Modifications of the isolated promoter sequences of the embodiments can provide for a range of expression of the heterologous nucleotide sequence. Thus, they may be modified to be weak promoters or strong promoters. Generally, a "weak promoter" is intended to mean a promoter that drives expression of a coding sequence at a low level. A "low level" of expression is intended to mean expression at levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts.

Fragments and variants of the disclosed promoter sequences are also encompassed. A "fragment" is intended to mean a portion of the promoter sequence. Fragments of a promoter sequence may retain biological activity and hence encompass fragments capable of driving tissue-preferred expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein. It is within skill in the art to determine whether such fragments decrease expression levels or alter the nature of expression, i.e., constitutive or inducible expression. Alternatively, fragments of a promoter nucleotide sequence that are useful as hybridization probes, such as described below, generally do not retain this regulatory activity. Thus, fragments of a nucleotide sequence may range from at least about 20 nucleotides, about 50 nucleotides, about 100 nucleotides, and up to the full-length of the nucleotide sequences disclosed herein.

Thus, a fragment of the maize ZM-027 promoter nucleotide sequence may encode a biologically active portion of the maize ZM-027 promoter or it may be a fragment that can be used as a hybridization probe or PCR primer using methods disclosed below. A biologically active portion of the maize ZM-027 promoter can be prepared by isolating a portion of one of the maize ZM-027 promoter nucleotide sequences and assessing the activity of that portion of the maize ZM-027 promoter. Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 1000 or up to the number of nucleotides present in the full-length promoter nucleotide sequence disclosed herein, e.g. 297 nucleotides for SEQ ID NO:1. For example, two specific fragments of the ZM-027 promoter which retain promoter activity are disclosed in the application as SEQ ID NOs: 2 and 3. The truncations of the promoter are 189 bp (SEQ ID NO 2) and 86 bp (SEQ ID NO 3) in length.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis and a procedure such as DNA "shuffling", are also encompassed by the compositions.

An "analogue" of the regulatory elements of the embodiments includes any substitution, deletion, or addition to the sequence of a regulatory element provided that said analogue maintains at least one regulatory property associated with the activity of the regulatory element of the embodiments. Such properties include directing organ or tissue preference, or a combination thereof, or temporal activity, or developmental activity, or a combination thereof.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence will have at least 40%, 50%, 60%, 65%, 70%, generally at least 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed. Biologically active variants include, for example, the native promoter sequence having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference.

Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438;

Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can be used to isolate corresponding sequences from other organisms, particularly other plants, for example, other monocots. In this manner, methods such as PCR, hybridization, and the like can be used to identify such sequences based on their sequence homology to the sequence set forth herein. Sequences isolated based on their sequence identity to the entire maize ZM-027 promoter sequence set forth herein or to fragments thereof are encompassed. The promoter regions of the embodiments may be isolated from any plant, including, but not limited to corn (*Zea mays*), *Brassica* (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Plants include corn, soybean, sunflower, safflower, *Brassica* or canola, wheat, barley, rye, alfalfa, and sorghum.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, supra. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the maize ZM-027 promoter sequences of the embodiments. Methods for preparation of probes for hybridization and for construction of cDNA and genomic libraries are generally known in the art and are disclosed in Sambrook, supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, often less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. for at least 30 minutes. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York), hereinafter "Ausubel". See also Sambrook supra.

Thus, isolated sequences that have tissue-preferred promoter activity and which hybridize under stringent conditions to the maize ZM-027 promoter sequences disclosed herein, or to fragments thereof, are encompassed.

In general, sequences that have promoter activity and hybridize to the promoter sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997): and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915).

Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the world wide web. Alignment may also be performed manually by inspection.

Unless otherwise stated, sequence identity/similarity values provided herein refer to the value obtained using the GAP program with default parameters, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP.

The GAP program uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, at least 80%, 90%, or 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, or 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The maize ZM-027 promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the embodiments to comprise, for example, plant cells, protoplasts, tissues, callus, embryos as well as flowers, stems, fruits, ovules, leaves, or roots originating in transgenic plants or their progeny previously transformed with a DNA molecule of the invention, and therefore consisting at least in part of transgenic cells.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the embodiments is generally as broad as the class of higher plants amenable to transformation techniques, including both monocotyledonous and dicotyledonous plants.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the embodiments include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a specific plant tissue, altering a plant's pathogen or insect defense mechanism, increasing the plant's tolerance to herbicides, altering tissue development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant.

It is recognized that any gene of interest can be operably linked to the promoter sequences disclosed herein and expressed in plant tissues.

A DNA construct comprising one of these genes of interest can be used with transformation techniques, such as those described below, to create disease or insect resistance in susceptible plant phenotypes or to enhance disease or insect resistance in resistant plant phenotypes. Accordingly, this disclosure encompasses methods that are directed to protecting plants against fungal pathogens, bacteria, viruses, nematodes, insects, and the like. By "disease resistance" or "insect resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products.

Pathogens of the embodiments include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Nematodes include parasitic nematodes such as root knot, cyst, and lesion nematodes, etc.

Genes encoding disease resistance traits include detoxification genes, such as against fumonisin (U.S. Pat. No. 5,792,931) avirulence (avr) and disease resistance (R) genes (Jones et al. (1994) *Science* 266:789; Martin et al. (1993) *Science* 262:1432; Mindrinos et al. (1994) *Cell* 78:1089); and the like. Insect resistance genes may encode resistance to pests that have great yield drag such as rootworm, cutworm, European corn borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or Basta® (glufosinate) (e.g., the bar gene), or other such genes known in the art. The bar gene encodes resistance to the herbicide Basta®, the nptII gene encodes resistance to the antibiotics kanamycin and geneticin, and the ALS gene encodes resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835, which discloses the nucleotide sequence of a form of EPSPS which can confer glyphosate resistance. U.S. Pat. No. 5,627,061 also describes genes encoding EPSPS enzymes. See also U.S. Pat. Nos. 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase. See, for example, U.S. patent application Ser. Nos. 10/004,357; and 10/427,692.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837-5847) facilitate expression of polyhydroxyalkanoates (PHAs).

Agronomically important traits that affect quality of grain, such as levels and types of oils, saturated and unsaturated, quality and quantity of essential amino acids, levels of cellulose, starch, and protein content can be genetically altered using the methods of the embodiments. Modifications include increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference. Another example is lysine and/or sulfur rich seed protein encoded by the soybean 2S albumin described in U.S. Pat. No. 5,850,016, and the chymotrypsin inhibitor from barley, Williamson et al. (1987) *Eur. J. Biochem.* 165:99-106, the disclosures of which are herein incorporated by reference.

Exogenous products include plant enzymes and products as well as those from other sources including prokaryotes and other eukaryotes. Such products include enzymes, cofactors, hormones, and the like.

Examples of other applicable genes and their associated phenotype include the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

"RNAi" refers to a series of related techniques to reduce the expression of genes (See for example U.S. Pat. No. 6,506, 559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The maize ZM-027 promoter sequence of the embodiments, and its related biologically active fragments or variants disclosed herein, may be used to drive expression of constructs that will result in RNA interference including microRNAs and siRNAs.

The heterologous nucleotide sequence operably linked to the maize ZM-027 promoter and related promoter sequences disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having at least 70%, 80%, or 85% or more sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in selected plant tissues.

In one embodiment, DNA constructs will comprise a transcriptional initiation region comprising one of the promoter nucleotide sequences disclosed herein, or variants or fragments thereof, operably linked to a heterologous nucleotide sequence whose expression is to be controlled by the tissue-preferred promoter of the embodiments. Such a DNA construct is provided with a plurality of restriction sites for insertion of the nucleotide sequence to be under the transcriptional regulation of the regulatory regions. The DNA construct may additionally contain selectable marker genes.

The DNA construct will include in the 5'-3' direction of transcription, a transcriptional initiation region (i.e., a tissue-preferred promoter of the embodiments), translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al., (1986) *Nucl. Acids Res.* 14:5641-5650; and An et al. (1989) *Plant Cell* 1:115-122, herein incorporated by reference in their entirety.

The DNA construct comprising a promoter sequence of the embodiments operably linked to a heterologous nucleotide sequence may also contain at least one additional nucleotide sequence for a gene to be cotransformed into the organism. Alternatively, the additional sequence(s) can be provided on another DNA construct.

Where appropriate, the heterologous nucleotide sequence whose expression is to be under the control of the tissue-preferred promoter sequence of the embodiments and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986) *Virology* 154:9-20); MDMV leader (Maize Dwarf Mosaic Virus); human immunoglobulin heavy-chain binding protein (BiP) (Macejak et al. (1991) *Nature* 353:90-94);

untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al. (1987) *Plant Physiology* 84:965-968. Other methods known to enhance translation and/or mRNA stability can also be utilized, for example, introns, such as the maize Ubiquitin intron (Christensen and Quail (1996) *Transgenic Res.* 5:213-218; Christensen et al. (1992) *Plant Molecular Biology* 18:675-689) or the maize AdhI intron (Kyozuka et al. (1991) *Mol. Gen. Genet.* 228:40-48; Kyozuka et al. (1990) *Maydica* 35:353-357), and the like.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the disclosure. Enhancers are known in the art and include the SV40 enhancer region, the 35S enhancer element, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications of the like may be made to the sequences of the embodiments. For this purpose, in vitro mutagenesis, primer repair, restriction, annealing, re-substitutions, for example, transitions and transversions, may be involved.

Reporter genes or selectable marker genes may be included in the DNA constructs. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518).

Other genes that could serve utility in the recovery of transgenic events but might not be required in the final product would include, but are not limited to, examples such as GUS (b-glucuronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):8115 and Luehrsen et al. (1992) *Methods Enzymol.* 216:397-414), and the maize genes encoding for anthocyanin production (Ludwig et al. (1990) *Science* 247:449).

The nucleic acid molecules of the embodiments are useful in methods directed to expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The methods of the embodiments are also directed to selectively expressing a nucleotide sequence in a plant tissue. Those methods comprise transforming a plant cell with a DNA construct comprising a promoter identified herein that initiates tissue-preferred transcription in a plant cell, operably linked to a heterologous nucleotide sequence, and regenerating a transformed plant from said plant cell.

The DNA construct comprising the particular promoter sequence of the embodiments operably linked to a nucleotide sequence of interest can be used to transform any plant. In this manner, genetically modified, i.e. transgenic or transformed, plants, plant cells, plant tissue, seed, root, and the like can be obtained.

Plant species suitable for the embodiments include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus* taeda), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow cedar (*Chamaecyparis nootkatensis*). Plants of the embodiments may be crop plants (for example, corn, alfalfa, sunflower, *Brassica*, soybean, cotton, safflower, peanut, sorghum, wheat, millet, tobacco, etc.) This disclosure is particularly suitable for any member of the monocot plant family including, but not limited to, maize, rice, barley, oats, wheat, sorghum, rye, sugarcane, pineapple, yams, onion, banana, coconut, and dates.

As used herein, "vector" refers to a DNA molecule such as a plasmid, cosmid, or bacterial phage for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the embodiments involve introducing a nucleotide construct into a plant. The term "introducing" is used herein to mean presenting to the plant the nucleotide construct in such a manner that the construct gains access to the interior of a cell of the plant. The methods of the embodiments do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the embodiments may be introduced into plants by contacting plants with a virus or viral nucleic acids. Generally, such methods involve incorporating a nucleotide construct of the embodiments within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,981,840 and 5,563,055), direct gene transfer (Paszkowski et al. (1984) *EMBO J.* 3:2717-2722), and ballistic particle acceleration (see, for example, U.S. Pat. Nos. 4,945,050; 5,879,918; 5,886,244; 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having tissue-preferred expression of the desired phenotypic characteristic identified. Two or more generations may be grown to ensure that tissue-preferred expression of the desired phenotypic characteristic is stably maintained and inherited and then seeds harvested to ensure tissue-preferred expression of the desired phenotypic characteristic has been achieved. Thus as used herein, "transformed seeds" refers to seeds that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants are generally self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polypeptide is cultivated using methods well known to one skilled in the art.

The embodiments provide compositions for screening compounds that modulate expression within selected tissues of embryos and plants. The vectors, cells, and plants can be used for screening candidate molecules for agonists and antagonists of the maize ZM-027 promoter. For example, a reporter gene can be operably linked to a maize ZM-027 promoter and expressed as a transgene in a plant. Compounds to be tested are added and reporter gene expression is measured to determine the effect on promoter activity.

The following examples are offered by way of illustration and not by way of limitation.

EXPERIMENTAL

The embodiments are further defined in the following Examples, in which parts and percentages are by weight and degrees are Celsius, unless otherwise stated. Techniques in molecular biology were typically performed as described in Ausubel or Sambrook, supra. It should be understood that these Examples, while indicating certain embodiments, are given by way of illustration only. From the above discussion and these Examples, one skilled in the art can ascertain the characteristics of the embodiments, and without departing from the spirit and scope thereof, can make various changes and modifications to the embodiments to adapt them to various usages and conditions. Thus, various modifications of the embodiments in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of the ZM-027 Gene as Part of a Search for a Silk-Preferred Promoter Candidate In order to generate resources for promoter discovery the following preparatory steps were taken. First, a proprietary maize transcriptome assembly dataset was created (UniCorn 5.0), representing most expressed maize genes, and encompassing cDNAs from more than a hundred tissue samples. Second, this UniCorn dataset was computationally analyzed with respect to gene ORF content to identify N-termini, or the start of the peptide coding regions. About 16,000 N-termini were so identified. Third, the N-termini regions were used to land on genomic DNA contigs (from the public maize B73 GSS assembly MAGI database 3.1 from about 850K GSS sequences, available on the Maize Assembled Genomic Island website run by Iowa State University, see also Fu Y et al. (2005) Proc. Nat. Acad. Sci., 102(34):12282-12287). In doing so, the upstream genomic regions for many of these genes were identified. These upstream regions were nominally treated as promoters for the initial discovery process, however it was recognized that some of these regions may correspond to 5'UTR transcribed regions.

Next, the transcripts were in turn related to the proprietary collection of MPSS mRNA profiling experiments. This demanded that the 17-nucleotide MPSS tags matched the transcript sequences bearing the N-termini. In this way the promoters were related through genes coding regions and to gene expression data. At this point a dataset of promoters with associated expression information were assembled. The gene expression data was key for determining interest in the promoter; that is, does the promoter belong to a gene with the expression pattern of interest. To facilitate the data-mining the MPSS gene expression data was further cataloged and curated to create a condense array of mean ppm values for key tissue types of interest. A wide variety of expression patterns of interest were pursued to identify MPSS tags with the desired expression pattern, and through which to the promoters of interest. For the purpose of this promoter invention, a query was conducted to find tags having their maximum ppm in a silk tissue. The maximum samples ppm must be at least 100 ppm. Discretional reductions were then made. Fifteen resulting tags were deemed moderately silk-preferred without necessary preference for expression post-pollination. Among these 15 was tag GATCGTTTCAGTATCAA. (Occurrence of this tag across tissues is summarized in Table 1. Occurrences are presented in ppm, or the number of times the tag was found in a particular tissue per one million sequence reads.) This tag in turn matched a gene the promoter of which was described as "ZmPromUTR__027 from MAGI__109352 398 nts". This gene was from UniCorn 5.0 contig pco516099, annotated per its best Swiss-Prot hit as "(P81651) Nonspecific lipid-transfer protein 1 (LTP 1)." It matched the MAGI genomic assembly MAGI__109352, from which the genomic sequence was derived (SEQ ID NO: 1). The ZM-027 derived promoter sequence is 297 bp long and contains a putative TATA box at −47. Precedence for activity of a relatively short promoter from a plant LTP in monocot floral tissue exists. A promoter from a non-related class I nsLTP from barley has been described that drives expression of heterologous genes in ovary and pericarp tissues (Federico et al. (2005) *Plant Mol. Biol.* 57:35-51).

TABLE 1

Summary of occurrence of MPSS tag for ZM-027 across maize tissues.

| Plant tissue type | Occurrence (ppm) |
|---|---|
| Root | 4.3 |
| Mesocotyl | 40 |
| Leaf | 767.8 |
| Stalk | 205.1 |
| Apical Meristem | 1567.8 |
| Immature Ear | 435.8 |
| Ovary | 1387.5 |
| Embryo | 165.5 |
| Endosperm | 0.7 |
| Pericarp | 962.7 |
| Silk | 2627.8 |
| Tassel Spikelet | 1081.5 |
| Pollen | 0 |

Example 2

Cloning of Promoter into Reporter Vector

The ZM-027 promoter (SEQ ID NO: 1) and the contiguous 5' UTR (SEQ ID NO: 4) was cloned from genomic DNA of public inbred A63 using PCR directly in front of the fluorescent protein DS-Red Express (Clontech). This construct was used in transient bombardment assays to define functionality of the promoter as described in Examples 3 and 4, and then converted to a format appropriate for stable maize transformation via *Agrobacterium* as outlined in Example 5.

Example 3

Silk Transient Assay

Non-pollinated ears from a highly transformable maize line were harvested from the greenhouse, and the extruded silk length was recorded. The husk was surface sterilized with 70% ethanol and the leaves peeled back, revealing the silks attached to the ear. The ear length was measured and explants were prepared within one hour after ear harvest. Attached silk explants were made up of 1 cm pieces of halved cob, with silks trimmed to 5 cm from the silk base. The media was 0.7% water agar, with or without 10 mg/L ascorbic acid. The explants were bombarded within two hours of harvest using a PDS-1000/He system (DuPont Company, Wilmington, Del., USA). For each marker construct used in these experiments, 5 µL of DNA (1 µg/µL) was precipitated with 50 µL of 2.5 M $CaCl_2$ and 20 µL of 0.1 M spermidine onto 50 µL of tungsten particles (1.0 µm at a particle density of 15 mg/mL).

Approximately 600 ng of DNA per shot was delivered at 650 psi under 27 in. Hg vacuum, 5 cm from the stopping plate. Two to three replicates per ear, and one to two ears per developmental stage were treated for each construct. The plates were sealed after bombardment and stored at 28-30° C. in the dark for 48 hours.

Forty-eight hours after bombardment, explants were examined for transgene expression. Explants bombarded with DS Red (Clontech) were observed at high magnification using a LEICA® microscope attached to a xenon light source, using an excitation of 557 nm and emission of 579 nm, to detect DS-Red Express expression. Micrographs were used to count the number of spots per explant, including the florets attached to the cob, and the area of the silks approximately 1 cm above the silk base. Results are listed below:

Example 4

Transient Analysis of Truncated Promoter Fragments

Three truncations of the ZM-027 promoter were used for transient analyses. In each case, the promoter fragment was fused 5' of the DS-Red Express fluorescent protein. These DNA constructs were shot as plasmids. The full-length ZM-027 promoter, extending 297 bp upstream of the 5'UTR, was analyzed, as were 2 truncations of 189 bp and 86 bp. The 5'UTR was included in the truncations. These experiments demonstrate that fragments of the promoter are functional, but at a significantly reduced level compared to the full length sequence. Bombardments were carried out as described in the methods below in two separate experiments with similar results each time. Results from a representative experiment are shown in Tables 2 and 3. Particles alone were the negative control, and showed no expression.

TABLE 2

Bombardment Assay Results for Promoter Truncations on Florets

| Construct | Florets counted per explant | Average spots per floret | Average floret spots per construct | % of full length ZM-027 expression |
|---|---|---|---|---|
| ZM-027 FL | 3 | 155 | | |
| | 3 | 141.3 | | |
| | 3 | 152 | 149.4 | 100% |
| ZM-027 FL | 3 | 86 | | |
| 189 bp | 3 | 97.3 | | |
| | 3 | 118 | 100.4 | 67% |
| ZM-027 FL | 3 | 71.7 | | |
| 86 bp | 3 | 54.7 | | |
| | 3 | 121.7 | 82.7 | 55% |
| Particles | 0 | 0 | 0 | 0% |

TABLE 3

Bombardment Assay Results for Promoter Truncations on Silks

| Construct | Silks counted per explant | Average spots per silk | Average silk spots per construct | % of full length ZM-027 expression |
|---|---|---|---|---|
| ZM-027 | 1 | 13 | | |
| FL | 2 | 21 | | |
| | 3 | 20.3 | 19.3 | 100% |
| ZM-027 | 2 | 14 | | |
| FL | 3 | 7.7 | | |
| 189 bp | 2 | 8 | 7 | 36% |
| ZM-027 | 2 | 5.5 | | |
| FL | 3 | 5.7 | | |
| 86 bp | 4 | 6 | 5.8 | 30% |
| Particles | 0 | 0 | 0 | 0% |

Example 5

Agrobacterium-Mediated Transformation of Maize and Regeneration of Transgenic Plants For Agrobacterium-mediated transformation of maize with a promoter sequence of the invention, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of Agrobacterium under conditions whereby the bacteria were capable of transferring the promoter sequence of the invention to at least one cell of at least one of the immature embryos (step 1: the infection step). In this step the immature embryos were immersed in an Agrobacterium suspension for the initiation of inoculation. The embryos were co-cultured for a time with the Agrobacterium (step 2: the co-cultivation step). The immature embryos were cultured on solid medium following the infection step. Following the co-cultivation period an optional "resting" step was performed. In this resting step, the embryos were incubated in the presence of at least one antibiotic known to inhibit the growth of Agrobacterium without the addition of a selective agent for plant transformants (step 3: resting step). The immature embryos were cultured on solid medium with antibiotic, but without a selecting agent, for elimination of Agrobacterium and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

Example 6

Stable Transgenic Activity of the ZM-027 Promoter (SEQ ID NO: 1) and the ZM-027 5' UTR Three T0 plants from each of fifteen events transformed with the ZM-027 promoter and 5' UTR (SEQ ID NO 1 and 4) driving DS-Red Express were grown in the greenhouse. One plant per event was used to assay seedling expression, one was used to assay expression at flowering and one was retained for T1 seed production. Positive control for expression was provided by plants transformed in parallel with the maize ubiquitin promoter driving DS-Red Express. Negative controls were T0 plants containing a maize ubiquitin promoter-PINII terminator construct absent any coding sequence. Expression was assessed microscopically as described for the transient assays in Example 3. The ability of the ZM-027 promoter-5'UTR cassette to direct DS-Red Express expression was analyzed in T0 maize seedling roots and leaf sheaths at the V5-V6 stage (Chase and Nanda (1967) Crop Sci 7:431-2). At flowering (or R1) stage, pollen; tassel spikelets; leaf blade, collar and sheath; husk; stalk node, pith and rind; silks; cob and female florets were analyzed for expression. Expression in kernels was assayed at 7 and 14 days after pollination (dap). No expression in seedling roots and leaf sheath was observed. At R1, very weak expression, or approximately 1/10 of that directed by the maize ubiquitin promoter, was observed in silks. No expression was seen in vegetative tissues (husk, leaf, stalks) or in pollen, tassel spikelets or cob. Significant expression was seen in female florets in the layer corresponding to the nucellus (equal to or greater than levels driven by the maize ubiquitin promoter). Slightly weaker expression was seen in the ovary walls. At 7 and 14 dap, very strong expression was seen in kernel pericarp, especially near the silk scar. Very strong expression (equal to or greater than that driven by the maize ubiquitin promoter) was also seen in the basal endosperm transfer cell (BETL) layer, just above the pedicel.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence, wherein said sequence initiates transcription in a plant cell, selected from the group consisting of:
   a) a nucleotide sequence comprising the sequence set forth in SEQ ID NO:3; and
   b) a nucleotide sequence comprising the plant promoter sequence comprised in Patent Deposit No. NRRL B-50159.

2. A DNA construct comprising the nucleotide sequence of claim 1 operably linked to a heterologous nucleotide sequence of interest.

3. A vector comprising the DNA construct of claim 2.

4. A plant cell having stably incorporated into its genome the DNA construct of claim 2.

5. The plant cell of claim 4, wherein said plant cell is from a monocot.

6. The plant cell of claim 5, wherein said monocot is maize.

7. The plant cell of claim 4, wherein said plant cell is from a dicot.

8. A plant having stably incorporated into its genome the DNA construct of claim 2.

9. The plant of claim 8, wherein said plant is a monocot.

10. The plant of claim 9, wherein said monocot is maize.

11. The plant of claim 8, wherein said plant is a dicot.

12. A transgenic seed of the plant of claim 8, wherein the seed comprises the DNA construct.

13. The plant of claim 8, wherein the heterologous nucleotide sequence of interest encodes a gene product that confers herbicide tolerance, herbicide resistance, salt tolerance, cold tolerance, drought resistance, pathogen resistance, or insect resistance.

* * * * *

SEQUENCE LISTING

```
<160> NUMBER OF SEQ ID NOS: 15

<210> SEQ ID NO 1
<211> LENGTH: 297
<212> TYPE: DNA
<213> ORGANISM: Zea Mays
<220> FEATURE:
<221> NAME/KEY: misc_feature
<222> LOCATION: (0)...(0)
<223> OTHER INFORMATION: ZM-027 promoter (full length)

<400> SEQUENCE: 1
tttatgggtg ccgcaggctt tgagctcttt tctactagtg aaagtagggc tatcgaaaca      60
ggtccacatg agccatgacc aaacgttgag agtgcagcta gcactgctac tctagctcgc     120
tgttaaaaga actcctacag gctacaggtg gtagtaatte accggagcga tgcatctacc     180
agcgaaccat cttaactcct ccctgaatg cactcaccca ccaccegtaa tagtaacttt     240 ccctccgcta tataaccccc acttgtgaaa ccctcgtatc cccacaacac cagaatc       297

<210> SEQ ID NO 2
<211> LENGTH: 189
<212> TYPE: DNA
<213> ORGANISM: Zea Mays
<220> FEATURE:
<221> NAME/KEY: misc_feature
<222> LOCATION: (0)...(0)
<223> OTHER INFORMATION: ZM-027-189 promoter (fragment)

<400> SEQUENCE: 2
actctagctc gctgttaaaa gaactcctac aggctacagg tggtagtaat tcaccggagc      60
gatgcatcta ccagcgaacc atcttaactc ctccctgaa tgcactcacc caccaccegt     120 aatagtaact ttccctccgc tataaccc ccacttgtga aaccctcgta tccccacaac     180
accagaatc                                                            189

<210> SEQ ID NO 3
<211> LENGTH: 86
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM-027-86 promoter (fragment)
```

<400> SEQUENCE: 3

```
actcacccac cacccgtaat agtaactttc cctccgctat ataaccccca cttgtgaaac    60
cctcgtatcc ccacaacacc agaatc                                        86
```

<210> SEQ ID NO 4
<211> LENGTH: 101
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM-027 5'UTR

<400> SEQUENCE: 4

```
cgcgaatcac agacgcgtct atctcagctt gctgcactgc actaccctgc cctgccatca    60
tatcgtacgt gagcccggcc gagcgagagc gagggagagg c                      101
```

<210> SEQ ID NO 5
<211> LENGTH: 935
<212> TYPE: DNA
<213> ORGANISM: Zea mays
<220> FEATURE:
<221> NAME/KEY: misc_feature
<222> LOCATION: (0)...(0)
<223> OTHER INFORMATION: ZM-027 unprocessed transcript

<400> SEQUENCE: 5

```
atggctgctc cgaagctcgc gacgctggcg ctggccgtgc tcctggcggc gaccgtggtg    60
gctccccgg ccgcggtgcg cgcggcgatg tcgtgctcca ccgtgtacag cacgctgatg   120
ccgtgcctgc cgttcgtcca gatgggcggg gccatgccgc ccagccgtg ctgcggcggc   180
atccgcagcc tgctgcagca ggccaacaac ccccgacc gccgcaccat ctgcggctgc   240
ctcaagaacg tcgccaacgg cgccaacggg agcggcacct acatcagccg cgccgccgcg   300
ctgcccagca agtgcggcgt cgccctgccg tacaagatca gcaccaacgt taactgcaac   360
acgtacgact gactacacac acgctcctgc atatatgccg tgttctctcg ttccaatact   420
gctctgcagc tagattatta ccattgcgct tgcgccggcc gttctgtgtt tctggactac   480
accgacgtgc tgtaaccttg tttctctctc tctgtttctc tttgcaggat taattaagtg   540
atgaggcgtc ctgtgcgcgt ccgggcgagg aatgcatgca tggcgctggc ggagagtaat   600
aaaataatgc tactggtatt ttaagctata tcgaggtgtg cctgtctcta gtcatttatt   660
atggtgttta ggaatggtct acacagttcg taacggtgta tcgtggatgc atgttgccgc   720
gagcagagta cgtaggcatg aaccgatgtg tgcgcttctg tctgtttact ctctctatgt   780
agtaatgtgt gggtgctttg atccagatgt attcgctcgt gagtcgtgga agtagatcgt   840
ttcagtatca ttaccgtgtg ttctttctta attttacatt cgattctgaa aatgaacatg   900
cacgaagctg gactggtcca gtatacgttg ccgca                             935
```

<210> SEQ ID NO 6
<211> LENGTH: 123
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM-027 propeptide sequence

<400> SEQUENCE: 6

```
Met Ala Ala Pro Lys Leu Ala Thr Leu Ala Leu Ala Val Leu Leu Ala
 1               5                  10                  15
```

Ala Thr Val Val Ala Pro Pro Ala Val Arg Ala Ala Met Ser Cys
              20                  25                  30

Ser Thr Val Tyr Ser Thr Leu Met Pro Cys Leu Pro Phe Val Gln Met
          35                  40                  45

Gly Gly Ala Met Pro Pro Gln Pro Cys Cys Gly Ile Arg Ser Leu
     50                  55                  60

Leu Gln Gln Ala Asn Asn Thr Pro Asp Arg Arg Thr Ile Cys Gly Cys
65              70                  75                  80

Leu Lys Asn Val Ala Asn Gly Ala Asn Gly Ser Gly Thr Tyr Ile Ser
              85                  90                  95

Arg Ala Ala Ala Leu Pro Ser Lys Cys Gly Val Ala Leu Pro Tyr Lys
              100                 105                 110

Ile Ser Thr Asn Val Asn Cys Asn Thr Ile Asn
              115                 120

<210> SEQ ID NO 7
<211> LENGTH: 95
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM-027 mature peptide sequence

<400> SEQUENCE: 7

Ala Met Ser Cys Ser Thr Val Tyr Ser Thr Leu Met Pro Cys Leu Pro
1               5                   10                  15

Phe Val Gln Met Gly Gly Ala Met Pro Pro Gln Pro Cys Cys Gly Gly
              20                  25                  30

Ile Arg Ser Leu Leu Gln Gln Ala Asn Asn Thr Pro Asp Arg Arg Thr
          35                  40                  45

Ile Cys Gly Cys Leu Lys Asn Val Ala Asn Gly Ala Asn Gly Ser Gly
     50                  55                  60

Thr Tyr Ile Ser Arg Ala Ala Ala Leu Pro Ser Lys Cys Gly Val Ala
65              70                  75                  80

Leu Pro Tyr Lys Ile Ser Thr Asn Val Asn Cys Asn Thr Ile Asn
              85                  90                  95

<210> SEQ ID NO 8
<211> LENGTH: 28
<212> TYPE: PRT
<213> ORGANISM: Zea mays
<220> FEATURE:
<221> NAME/KEY: PEPTIDE
<222> LOCATION: (0)...(0)
<223> OTHER INFORMATION: ZM-027 signal peptide sequence

<400> SEQUENCE: 8

Met Ala Ala Pro Lys Leu Ala Thr Leu Ala Leu Ala Val Leu Leu Ala
1               5                   10                  15

Ala Thr Val Val Ala Pro Pro Ala Ala Val Arg Ala
              20                  25

<210> SEQ ID NO 9
<211> LENGTH: 120
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os01g0822900

<400> SEQUENCE: 9

Met Ala Pro Arg Cys Ala Thr Leu Ala Val Val Val Leu Val Ala
1               5                   10                  15

Ala Val Val Ala Pro Pro Thr Ala Val Arg Ala Ala Ile Ser Cys Ser
            20                  25                  30

Ala Val Tyr Asn Thr Leu Met Pro Cys Leu Pro Tyr Val Gln Ala Gly
        35                  40                  45

Gly Thr Val Pro Arg Ala Cys Cys Gly Gly Ile Gln Ser Leu Leu Ala
    50                  55                  60

Ala Ala Asn Asn Thr Pro Asp Arg Arg Thr Ile Cys Gly Cys Leu Lys
65                  70                  75                  80

Asn Val Ala Asn Gly Ala Ser Gly Pro Tyr Ile Thr Arg Ala Ala
                85                  90                  95

Ala Leu Pro Ser Lys Cys Asn Val Ser Leu Pro Tyr Lys Ile Ser Thr
            100                 105                 110

Ser Val Asn Cys Asn Ala Ile Asn
        115                 120

<210> SEQ ID NO 10
<211> LENGTH: 138
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Os05g0477900

<400> SEQUENCE: 10

Met Val Pro Ala Ala Arg Ser Gly Trp Pro Ala Ala Ala Val Leu
1               5                   10                  15

Val Val Val Leu Val Leu Ser Ser Pro Pro Gly Thr Ser Thr Val Val
            20                  25                  30

Val Ala Arg Ala Ala Leu Ser Cys Ser Thr Val Tyr Asn Thr Leu Leu
        35                  40                  45

Pro Cys Leu Pro Tyr Val Gln Ser Gly Gly Ala Val Pro Ala Ala Cys
    50                  55                  60

Cys Gly Gly Ile Arg Ser Val Ala Ala Arg Thr Thr Ala Asp
65                  70                  75                  80

Arg Arg Ala Ala Cys Thr Cys Leu Lys Asn Val Ala Ala Gly Ala Ala
                85                  90                  95

Gly Gly Pro Tyr Ile Ser Arg Ala Ala Gly Leu Pro Gly Arg Cys Gly
            100                 105                 110

Val Ser Val Pro Phe Lys Ile Ser Pro Asn Val Asn Cys Asn Ala Tyr
        115                 120                 125

Val Lys Thr Lys Asn Gln Ile Asn Leu Tyr
    130                 135

<210> SEQ ID NO 11
<211> LENGTH: 121
<212> TYPE: PRT
<213> ORGANISM: Hordeum vulgare
<220> FEATURE:
<221> NAME/KEY: PEPTIDE
<222> LOCATION: (0)...(0)
<223> OTHER INFORMATION: gb_AAF14232.1

<400> SEQUENCE: 11

Met Ala Ala Pro Arg Gly Ala Ala Leu Val Leu Ala Met Val Leu Ala
1               5                   10                  15

-continued

```
Ala Met Val Val Ala Pro Pro Val Thr Val Arg Ala Ala Ile Ser Cys
            20                  25                  30

Ser Ala Val Tyr Ser Thr Leu Met Pro Cys Leu Gln Tyr Val Gln Gln
            35                  40                  45

Gly Gly Thr Pro Ala Arg Gly Cys Cys Ala Gly Ile Gln Asn Leu Leu
        50                  55                  60

Ala Glu Ala Asn Asn Ser Pro Asp Arg Arg Thr Ile Cys Gly Cys Leu
 65                  70                  75                  80

Lys Asn Val Ala Asn Ala Ala Pro Gly Gly Ser Glu Ile Thr Arg Ala
                85                  90                  95

Ala Ala Leu Pro Ser Lys Cys Asn Val Asn Leu Pro Tyr Lys Ile Ser
            100                 105                 110

Pro Ser Val Asp Cys Asn Ser Ile His
            115                 120

<210> SEQ ID NO 12
<211> LENGTH: 121
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: TaLtp9.7c;CAH69197.1

<400> SEQUENCE: 12

Met Ala Ala Pro Arg Gly Ala Ala Val Val Leu Ala Met Val Leu Ala
 1               5                  10                  15

Ala Met Val Val Ala Pro Pro Ala Thr Val His Ala Ala Ile Ser Cys
            20                  25                  30

Ser Thr Val Tyr Ser Thr Leu Met Pro Cys Leu Gln Tyr Val Gln Gln
            35                  40                  45

Gly Gly Ser Pro Ala Arg Gly Cys Cys Thr Gly Ile Gln Asn Leu Leu
        50                  55                  60

Ala Glu Ala Asn Asn Ser Pro Asp Arg Arg Thr Ile Cys Gly Cys Leu
 65                  70                  75                  80

Lys Asn Val Ala Asn Gly Ala Ser Gly Gly Pro Tyr Ile Thr Arg Ala
                85                  90                  95

Ala Ala Leu Pro Ser Lys Cys Asn Val Ala Leu Pro Tyr Lys Ile Ser
            100                 105                 110

Pro Ser Val Asp Cys Asn Ser Ile His
            115                 120

<210> SEQ ID NO 13
<211> LENGTH: 120
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: TaLtp9.7b; CAH69196.1

<400> SEQUENCE: 13

Met Ala Ala Pro Arg Gly Ala Ala Leu Val Leu Ala Met Val Leu Ala
 1               5                  10                  15

Ala Met Val Val Ala Pro Pro Ala Thr Val His Ala Ile Ser Cys Ser
            20                  25                  30

Thr Val Tyr Ser Thr Leu Met Pro Cys Leu Gln Tyr Val Gln Gln Gly
        35                  40                  45

Gly Ser Pro Ala Arg Gly Cys Cys Thr Gly Ile Gln Asn Leu Leu Ala
    50                  55                  60
```

```
Glu Ala Asn Asn Ser Pro Asp Arg Arg Thr Ile Cys Gly Cys Leu Lys
 65                  70                  75                  80

Asn Val Ala Asn Gly Ala Ser Gly Gly Pro Tyr Ile Thr Arg Ala Ala
                 85                  90                  95

Ala Leu Pro Ser Lys Cys Asn Val Ala Leu Pro Tyr Lys Ile Ser Pro
            100                 105                 110

Ser Val Asp Cys Asn Ser Ile His
        115                 120
```

<210> SEQ ID NO 14
<211> LENGTH: 120
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: TaLtp9.7d; CAH69198.1

<400> SEQUENCE: 14

```
Met Ala Ala Pro Arg Gly Ala Ala Leu Val Leu Ala Met Val Leu Ala
  1               5                  10                  15

Ala Met Leu Val Ala Pro Pro Ala Thr Val His Ala Ile Ser Cys Ser
                 20                  25                  30

Thr Val Tyr Ser Thr Leu Met Pro Cys Leu Gln Tyr Val Gln Gln Gly
             35                  40                  45

Gly Ser Pro Ala Arg Gly Cys Cys Thr Gly Ile Gln Asn Leu Leu Ala
         50                  55                  60

Glu Ala Asn Asn Ser Pro Asp Arg Arg Thr Ile Cys Gly Cys Leu Lys
 65                  70                  75                  80

Asn Val Ala Asn Gly Ala Ser Gly Gly Pro Tyr Ile Thr Arg Ala Ala
                 85                  90                  95

Ala Leu Pro Ser Lys Cys Asn Val Ala Leu Pro Tyr Lys Ile Ser Pro
            100                 105                 110

Ser Val Asp Cys Asn Ser Ile His
        115                 120
```

<210> SEQ ID NO 15
<211> LENGTH: 120
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: TaLtp9.7e; CAH69210.1

<400> SEQUENCE: 15

```
Met Ala Ala Pro Arg Gly Ala Ala Leu Val Leu Ala Met Val Leu Ala
  1               5                  10                  15

Ala Met Leu Val Ala Pro Pro Ala Thr Val His Ala Ile Ser Cys Ser
                 20                  25                  30

Thr Val Tyr Ser Thr Leu Met Pro Cys Leu Gln Tyr Val Gln Gln Gly
             35                  40                  45

Gly Ser Pro Ala Arg Gly Cys Cys Thr Gly Ile Gln Asn Leu Leu Val
         50                  55                  60

Glu Ala Asn Asn Ser Pro Asp Arg Arg Thr Ile Cys Gly Cys Leu Glu
 65                  70                  75                  80

Asn Val Ala Asn Gly Ala Ser Gly Gly Pro Tyr Ile Thr Arg Ala Ala
                 85                  90                  95

Ala Leu Pro Ser Lys Cys Asn Val Ala Leu Pro Tyr Lys Ile Ser Pro
```

-continued

```
                100             105             110
Ser Val Asp Cys Asn Ser Ile His
            115             120
```